(12) United States Patent
Quadri

(10) Patent No.: US 9,433,514 B2
(45) Date of Patent: Sep. 6, 2016

(54) METHOD OF SECURING A PROSTHESIS

(75) Inventor: Arshad Quadri, West Hartford, CT (US)

(73) Assignee: Edwards Lifesciences CardiAQ LLC, Irvine, CA (US)

(*) Notice: Subject to any disclaimer, the term of this patent is extended or adjusted under 35 U.S.C. 154(b) by 0 days.

(21) Appl. No.: 13/346,593

(22) Filed: Jan. 9, 2012

(65) Prior Publication Data
US 2012/0179239 A1 Jul. 12, 2012

Related U.S. Application Data

(63) Continuation of application No. 12/084,586, filed as application No. PCT/US2006/043526 on Nov. 9, 2006, now Pat. No. 8,092,520.

(60) Provisional application No. 60/735,221, filed on Nov. 10, 2005.

(51) Int. Cl.
*A61F 2/24* (2006.01)
*A61F 2/82* (2013.01)
(Continued)

(52) U.S. Cl.
CPC ............. *A61F 2/82* (2013.01); *A61F 2/2418* (2013.01); *A61F 2/915* (2013.01); *A61F 2002/8483* (2013.01); *A61F 2002/8486* (2013.01); *A61F 2002/91541* (2013.01); *A61F 2002/91558* (2013.01); *A61F 2220/0016* (2013.01); *A61F 2230/0013* (2013.01); *A61F 2230/0054* (2013.01)

(58) Field of Classification Search
CPC .................................................. A61F 2/2418
USPC ...................................... 623/1.15, 1.16, 1.36
See application file for complete search history.

(56) References Cited

U.S. PATENT DOCUMENTS

| 865,203 A | 9/1907 | Mustonen et al. |
|---|---|---|
| 3,657,744 A | 4/1972 | Ersek |
| 3,671,979 A | 6/1972 | Moulopoulos |

(Continued)

FOREIGN PATENT DOCUMENTS

| CA | 2304325 A1 | 10/2000 |
|---|---|---|
| DE | 3128704 | 2/1983 |

(Continued)

OTHER PUBLICATIONS

Grube, Eberhard, MD, et al., "Percutaneous Implantation of the CoreValve Self-Expanding Valve Prosthesis in High-Risk Patients With Aortic Valve Disease, The Siegburg First-in-Man Study" Journal of the American Heart Association, 2006; 114:1616-1624, originally published online Oct. 2, 2006.

(Continued)

*Primary Examiner* — Thomas J Sweet
*Assistant Examiner* — Megan Wolf
(74) *Attorney, Agent, or Firm* — Knobbe Martens Olson & Bear LLP

(57) ABSTRACT

A method of securing a prosthesis atraumatically to body tissue can include one or more of the following steps. A prosthesis can be delivered into a patient. The prosthesis may include an expandable frame. The frame can be expanded within a body cavity of the patient. Expansion of the frame can causes respective ends of both proximal prongs and distal prongs to draw closer together to grasp native tissue between the respective ends of the proximal prongs and distal prongs.

20 Claims, 12 Drawing Sheets

(51) Int. Cl.
*A61F 2/915* (2013.01)
*A61F 2/848* (2013.01)

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,733,665 A | 3/1988 | Palmaz |
| 4,776,337 A | 10/1988 | Palmaz |
| 4,777,951 A | 10/1988 | Cribier et al. |
| 4,865,600 A | 9/1989 | Carpentier et al. |
| 4,950,227 A | 8/1990 | Savin et al. |
| 4,994,077 A | 2/1991 | Dobben |
| 5,197,978 A | 3/1993 | Hess |
| 5,326,371 A | 7/1994 | Love et al. |
| 5,332,402 A | 7/1994 | Teitelbaum |
| 5,344,427 A | 9/1994 | Cottenceau et al. |
| 5,370,685 A | 12/1994 | Stevens |
| 5,397,355 A | 3/1995 | Marin |
| 5,411,552 A | 5/1995 | Andersen et al. |
| 5,415,667 A | 5/1995 | Frater |
| 5,439,446 A | 8/1995 | Barry |
| 5,474,563 A | 12/1995 | Myler |
| 5,545,214 A | 8/1996 | Stevens |
| 5,554,185 A | 9/1996 | Block et al. |
| 5,575,818 A | 11/1996 | Pinchuk |
| 5,607,444 A | 3/1997 | Lam |
| 5,669,919 A | 9/1997 | Sanders et al. |
| 5,697,382 A | 12/1997 | Love et al. |
| D390,957 S | 2/1998 | Fontaine |
| 5,725,519 A | 3/1998 | Penner |
| 5,769,812 A | 6/1998 | Stevens et al. |
| 5,807,398 A | 9/1998 | Shaknovich |
| 5,810,873 A | 9/1998 | Morales |
| 5,840,081 A | 11/1998 | Andersen et al. |
| 5,855,601 A | 1/1999 | Bessler et al. |
| 5,868,777 A | 2/1999 | Lam |
| 5,868,782 A | 2/1999 | Frantzen |
| 5,879,381 A | 3/1999 | Moriuch et al. |
| 5,902,334 A | 5/1999 | Dwyer et al. |
| 5,935,108 A | 8/1999 | Katoh |
| 5,954,764 A | 9/1999 | Parodi |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,053,940 A | 4/2000 | Wijay |
| 6,086,612 A | 7/2000 | Jansen |
| 6,113,612 A * | 9/2000 | Swanson et al. ............ 623/1.15 |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt |
| 6,168,614 B1 | 1/2001 | Andersen et al. |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,425,916 B1 | 7/2002 | Garrison et al. |
| 6,440,164 B1 | 8/2002 | DiMatteo et al. |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,517,573 B1 | 2/2003 | Pollock |
| 6,527,800 B1 | 3/2003 | McGuckin, Jr. et al. |
| 6,551,303 B1 | 4/2003 | Van Tassei et al. |
| 6,582,462 B1 | 6/2003 | Andersen et al. |
| 6,602,281 B1 | 8/2003 | Klein |
| 6,610,088 B1 | 8/2003 | Gabbay |
| 6,641,606 B2 | 11/2003 | Ouriel et al. |
| 6,652,578 B2 | 11/2003 | Bailey et al. |
| D484,979 S | 1/2004 | Fontaine |
| 6,676,698 B2 | 1/2004 | McGuckin et al. |
| 6,682,537 B2 | 1/2004 | Ouriel et al. |
| 6,695,878 B2 | 2/2004 | McGuckin et al. |
| 6,712,836 B1 | 3/2004 | Berg et al. |
| 6,730,118 B2 | 5/2004 | Spenser et al. |
| 6,733,523 B2 | 5/2004 | Shaolian et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 6,979,350 B2 | 12/2005 | Moll et al. |
| 7,014,653 B2 | 3/2006 | Ouriel et al. |
| 7,018,401 B1 | 3/2006 | Hyodoh et al. |
| 7,018,406 B2 | 3/2006 | Seguin et al. |
| 7,025,780 B2 | 4/2006 | Gabbay |
| 7,044,962 B2 | 5/2006 | Elliott |
| 7,087,088 B2 | 8/2006 | Berg et al. |
| 7,147,660 B2 | 12/2006 | Chobotov et al. |
| 7,147,661 B2 * | 12/2006 | Chobotov et al. ............ 623/1.16 |
| 7,153,322 B2 | 12/2006 | Alt |
| 7,186,265 B2 | 3/2007 | Sharkawy et al. |
| 7,198,646 B2 | 4/2007 | Figulla et al. |
| 7,201,772 B2 | 4/2007 | Schwammenthal et al. |
| D553,747 S | 10/2007 | Fliedner |
| 7,276,078 B2 | 10/2007 | Spenser et al. |
| 7,276,084 B2 | 10/2007 | Yang et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salaheih et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,585,321 B2 | 9/2009 | Cribier |
| 7,608,114 B2 | 10/2009 | Levine et al. |
| 7,618,446 B2 | 11/2009 | Andersen et al. |
| 7,628,805 B2 | 12/2009 | Spenser et al. |
| 7,632,298 B2 | 12/2009 | Hijlkema et al. |
| 7,748,389 B2 | 7/2010 | Salahieh et al. |
| 7,771,463 B2 | 8/2010 | Ton et al. |
| 7,771,472 B2 | 8/2010 | Hedricksen et al. |
| 7,785,360 B2 | 8/2010 | Freitag |
| 7,803,185 B2 | 9/2010 | Gabbay |
| 7,815,589 B2 | 10/2010 | Meade et al. |
| 7,824,443 B2 | 11/2010 | Salahieh et al. |
| 7,871,435 B2 | 1/2011 | Carpentier |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,377 B2 | 7/2011 | Lane |
| 8,016,870 B2 | 9/2011 | Chew et al. |
| 8,016,877 B2 | 9/2011 | Seguin et al. |
| 8,048,153 B2 | 11/2011 | Salahieh et al. |

(56) References Cited

U.S. PATENT DOCUMENTS

| | | |
|---|---|---|
| 8,052,750 B2 | 11/2011 | Tuval et al. |
| 8,070,800 B2 | 12/2011 | Lock et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino |
| 8,167,926 B2 | 5/2012 | Hartley et al. |
| 8,167,932 B2 | 5/2012 | Bourang et al. |
| 8,167,934 B2 | 5/2012 | Styrc et al. |
| 8,177,799 B2 | 5/2012 | Orban, III |
| 8,182,528 B2 | 5/2012 | Salahieh et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,221,482 B2 | 7/2012 | Cottone et al. |
| 8,221,493 B2 | 7/2012 | Boyle et al. |
| 8,226,710 B2 | 7/2012 | Nguyen et al. |
| 8,246,675 B2 | 8/2012 | Zegdi |
| 8,246,678 B2 | 8/2012 | Salahieh et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,317,854 B1 | 11/2012 | Ryan et al. |
| 8,337,541 B2 | 12/2012 | Quadri et al. |
| 8,361,137 B2 | 1/2013 | Perouse |
| 8,361,537 B2 | 1/2013 | Shanley |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,449,599 B2 | 5/2013 | Chau et al. |
| 8,500,798 B2 | 8/2013 | Rowe et al. |
| 8,579,965 B2 | 11/2013 | Bonhoeffer et al. |
| 8,585,749 B2 | 11/2013 | Shelso |
| 8,585,756 B2 | 11/2013 | Bonhoeffer et al. |
| 8,591,570 B2 | 11/2013 | Revuelta et al. |
| 8,617,236 B2 | 12/2013 | Paul et al. |
| 8,652,201 B2 | 2/2014 | Oberti et al. |
| 8,652,203 B2 | 2/2014 | Quadri et al. |
| 8,668,733 B2 | 3/2014 | Haug et al. |
| 8,679,174 B2 | 3/2014 | Ottma et al. |
| 8,685,086 B2 | 4/2014 | Navia et al. |
| 8,707,957 B2 | 4/2014 | Callister et al. |
| 8,721,707 B2 | 5/2014 | Boucher et al. |
| 8,721,708 B2 | 5/2014 | Sequin et al. |
| 8,740,974 B2 | 6/2014 | Lambrecht et al. |
| 8,747,460 B2 | 6/2014 | Tuval et al. |
| 8,753,384 B2 | 6/2014 | Leanna |
| 8,758,432 B2 | 6/2014 | Solem |
| 8,771,345 B2 | 7/2014 | Tuval et al. |
| 8,771,346 B2 | 7/2014 | Tuval et al. |
| 8,777,975 B2 | 7/2014 | Kashkarov et al. |
| 8,784,478 B2 | 7/2014 | Tuval et al. |
| 8,795,356 B2 | 8/2014 | Quadri et al. |
| 8,828,078 B2 | 9/2014 | Salahieh et al. |
| 8,834,564 B2 | 9/2014 | Tuval et al. |
| 8,894,702 B2 | 11/2014 | Quadri et al. |
| 8,911,455 B2 | 12/2014 | Quadri et al. |
| 8,961,583 B2 | 2/2015 | Hojeibane et al. |
| 8,979,922 B2 | 3/2015 | Jayasinghe et al. |
| 8,992,608 B2 | 3/2015 | Haug et al. |
| 8,998,979 B2 | 4/2015 | Seguin et al. |
| 9,005,273 B2 | 4/2015 | Salahieh et al. |
| 9,011,521 B2 | 4/2015 | Haug et al. |
| 9,023,100 B2 | 5/2015 | Quadri et al. |
| 9,028,545 B2 | 5/2015 | Taylor |
| 9,138,312 B2 | 9/2015 | Tuval et al. |
| 2001/0007956 A1 | 7/2001 | Letac et al. |
| 2001/0021872 A1 | 9/2001 | Bailey et al. |
| 2001/0047180 A1 | 11/2001 | Grudem et al. |
| 2001/0047200 A1 | 11/2001 | White |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0055772 A1 | 5/2002 | McGuckin et al. |
| 2002/0111619 A1 | 8/2002 | Keast et al. |
| 2002/0183827 A1 | 12/2002 | Derus et al. |
| 2003/0040792 A1* | 2/2003 | Gabbay ................ 623/2.11 |
| 2003/0105517 A1 | 6/2003 | White et al. |
| 2003/0114913 A1 | 6/2003 | Spenser et al. |
| 2003/0120263 A1 | 6/2003 | Ouriel et al. |
| 2003/0120330 A1 | 6/2003 | Ouriel et al. |
| 2003/0120333 A1 | 6/2003 | Ouriel et al. |
| 2003/0130729 A1 | 7/2003 | Paniagua |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0039436 A1 | 2/2004 | Spenser et al. |
| 2004/0087900 A1 | 5/2004 | Thompson et al. |
| 2004/0093058 A1 | 5/2004 | Cottone et al. |
| 2004/0093060 A1 | 5/2004 | Seguin et al. |
| 2004/0102842 A1 | 5/2004 | Jansen |
| 2004/0117009 A1 | 6/2004 | Cali et al. |
| 2004/0133273 A1 | 7/2004 | Cox |
| 2004/0186561 A1 | 9/2004 | McGuckin, Jr. et al. |
| 2004/0193261 A1 | 9/2004 | Berreklou |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin, Jr. et al. |
| 2004/0236411 A1 | 11/2004 | Sarac et al. |
| 2004/0243230 A1 | 12/2004 | Navia et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0125020 A1 | 6/2005 | Meade et al. |
| 2005/0137682 A1 | 6/2005 | Justino |
| 2005/0137686 A1 | 6/2005 | Salahieh et al. |
| 2005/0137687 A1* | 6/2005 | Salahieh et al. .......... 623/2.11 |
| 2005/0137690 A1 | 6/2005 | Salahieh et al. |
| 2005/0137691 A1 | 6/2005 | Salahieh et al. |
| 2005/0137693 A1 | 6/2005 | Haug et al. |
| 2005/0137695 A1 | 6/2005 | Salahieh et al. |
| 2005/0137701 A1 | 6/2005 | Salahieh et al. |
| 2005/0154444 A1 | 7/2005 | Quadri |
| 2005/0159811 A1 | 7/2005 | Lane |
| 2005/0182486 A1 | 8/2005 | Gabbay |
| 2005/0216079 A1 | 9/2005 | Macoviak |
| 2005/0234546 A1 | 10/2005 | Nugent et al. |
| 2005/0283231 A1 | 12/2005 | Haug et al. |
| 2006/0020247 A1 | 1/2006 | Kagan et al. |
| 2006/0020327 A1 | 1/2006 | Lashinski et al. |
| 2006/0020334 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0106454 A1 | 5/2006 | Osborne et al. |
| 2006/0116625 A1 | 6/2006 | Renati et al. |
| 2006/0129235 A1 | 6/2006 | Seguin et al. |
| 2006/0149360 A1 | 7/2006 | Schwammenthal et al. |
| 2006/0161265 A1 | 7/2006 | Levine et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0253191 A1 | 11/2006 | Salahieh et al. |
| 2006/0259135 A1* | 11/2006 | Navia et al. .............. 623/2.11 |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0010876 A1 | 1/2007 | Salaheih et al. |
| 2007/0016286 A1 | 1/2007 | Herrmann et al. |
| 2007/0043435 A1 | 2/2007 | Seguin et al. |
| 2007/0050021 A1 | 3/2007 | Johnson |
| 2007/0067016 A1 | 3/2007 | Jung |
| 2007/0100432 A1 | 5/2007 | Case et al. |
| 2007/0118206 A1 | 5/2007 | Colgan et al. |
| 2007/0123798 A1 | 5/2007 | Rahamimov |
| 2007/0129794 A1 | 6/2007 | Realyvasquez |

(56) References Cited

U.S. PATENT DOCUMENTS

| | | |
|---|---|---|
| 2007/0142906 A1 | 6/2007 | Figulla et al. |
| 2007/0162107 A1 | 7/2007 | Salahieh et al. |
| 2007/0213813 A1 | 9/2007 | Von Segesser et al. |
| 2007/0219620 A1 | 9/2007 | Eells et al. |
| 2007/0233228 A1 | 10/2007 | Eberhardt et al. |
| 2007/0250151 A1 | 10/2007 | Pereira |
| 2007/0255391 A1 | 11/2007 | Hojeibane et al. |
| 2007/0255394 A1 | 11/2007 | Ryan |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0082164 A1 | 4/2008 | Friedman |
| 2008/0082166 A1 | 4/2008 | Styrc et al. |
| 2008/0087581 A1 | 4/2008 | Shanley |
| 2008/0097571 A1 | 4/2008 | Denison et al. |
| 2008/0125853 A1 | 5/2008 | Boyle et al. |
| 2008/0125859 A1 | 5/2008 | Salaheih et al. |
| 2008/0133003 A1 | 6/2008 | Seguin |
| 2008/0140189 A1 | 6/2008 | Nguyen et al. |
| 2008/0147183 A1 | 6/2008 | Styrc |
| 2008/0161911 A1 | 7/2008 | Revuelta et al. |
| 2008/0183273 A1 | 7/2008 | Mesana et al. |
| 2008/0208307 A1 | 8/2008 | Ben-Muvhar et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243233 A1 | 10/2008 | Ben-Muvhar et al. |
| 2008/0243245 A1 | 10/2008 | Thambar et al. |
| 2008/0269878 A1 | 10/2008 | Iobbi |
| 2009/0005863 A1 | 1/2009 | Goetz et al. |
| 2009/0062908 A1 | 3/2009 | Bonhoeffer et al. |
| 2009/0076598 A1 | 3/2009 | Salaheih et al. |
| 2009/0088832 A1 | 4/2009 | Chew et al. |
| 2009/0138079 A1 | 5/2009 | Tuval et al. |
| 2009/0149946 A1 | 6/2009 | Dixon |
| 2009/0177262 A1 | 7/2009 | Oberti et al. |
| 2009/0188964 A1 | 7/2009 | Orlov |
| 2009/0192601 A1 | 7/2009 | Rafiee et al. |
| 2009/0216314 A1 | 8/2009 | Quadri |
| 2009/0234443 A1 | 9/2009 | Ottma et al. |
| 2009/0248132 A1 | 10/2009 | Bloom et al. |
| 2009/0248133 A1 | 10/2009 | Bloom et al. |
| 2009/0264997 A1 | 10/2009 | Salaheih et al. |
| 2009/0270972 A1 | 10/2009 | Lane |
| 2009/0287299 A1 | 11/2009 | Tabor et al. |
| 2009/0306768 A1 | 12/2009 | Quadri |
| 2010/0004740 A1 | 1/2010 | Seguin et al. |
| 2010/0036479 A1 | 2/2010 | Hill et al. |
| 2010/0082089 A1 | 4/2010 | Quadri et al. |
| 2010/0082094 A1 | 4/2010 | Quadri et al. |
| 2010/0114299 A1 | 5/2010 | Ben Muvhar et al. |
| 2010/0179647 A1 | 7/2010 | Carpenter et al. |
| 2010/0298931 A1 | 11/2010 | Quadri et al. |
| 2011/0022157 A1 | 1/2011 | Essinger et al. |
| 2011/0029067 A1 | 2/2011 | McGuckin, Jr. et al. |
| 2011/0178597 A9 | 7/2011 | Navia et al. |
| 2011/0313515 A1 | 12/2011 | Quadri et al. |
| 2012/0041550 A1 | 2/2012 | Salahieh et al. |
| 2012/0059452 A1 | 3/2012 | Boucher et al. |
| 2012/0078353 A1 | 3/2012 | Quadri et al. |
| 2012/0215303 A1 | 8/2012 | Quadri et al. |
| 2012/0290062 A1 | 11/2012 | McNamara et al. |
| 2013/0006294 A1 | 1/2013 | Kashkarov |
| 2013/0110227 A1 | 5/2013 | Quadri et al. |
| 2013/0131788 A1 | 5/2013 | Quadri et al. |
| 2013/0131793 A1 | 5/2013 | Quadri et al. |
| 2013/0138203 A1 | 5/2013 | Quadri et al. |
| 2013/0138207 A1 | 5/2013 | Quadri et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0184813 A1 | 7/2013 | Quadri et al. |
| 2014/0052242 A1 | 2/2014 | Revuelta et al. |
| 2014/0172085 A1 | 6/2014 | Quadri et al. |
| 2014/0172086 A1 | 6/2014 | Quadri et al. |
| 2014/0214153 A1 | 7/2014 | Ottma et al. |
| 2014/0236288 A1 | 8/2014 | Lambrecht et al. |
| 2014/0277390 A1 | 9/2014 | Ratz et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0309728 A1 | 10/2014 | Dehdashtian et al. |
| 2014/0309731 A1 | 10/2014 | Quadri et al. |
| 2014/0309732 A1 | 10/2014 | Solem |
| 2014/0379077 A1 | 12/2014 | Tuval et al. |
| 2015/0012085 A1 | 1/2015 | Salahieh et al. |
| 2015/0018938 A1 | 1/2015 | Von Segesser et al. |
| 2015/0032153 A1 | 1/2015 | Quadri et al. |
| 2015/0066140 A1 | 3/2015 | Quadri |
| 2015/0081009 A1 | 3/2015 | Quadri |
| 2015/0157458 A1 | 6/2015 | Thambar et al. |
| 2015/0238315 A1 | 8/2015 | Rabito et al. |
| 2015/0305864 A1 | 10/2015 | Quadri et al. |
| 2015/0328000 A1 | 11/2015 | Ratz et al. |
| 2015/0342736 A1 | 12/2015 | Rabito et al. |

FOREIGN PATENT DOCUMENTS

| | | |
|---|---|---|
| DE | 10 2006 052 564 | 12/2007 |
| EP | 0 657 147 | 6/1995 |
| EP | 1 47 996 B1 | 11/2004 |
| EP | 1 255 510 B1 | 4/2007 |
| EP | 1 772 104 A2 | 4/2007 |
| GB | 1 264 471 | 2/1972 |
| GB | 1315 844 | 5/1973 |
| GB | 2245495 | 1/1992 |
| GB | 2 398 245 | 8/2004 |
| JP | 2002-540889 | 12/2002 |
| JP | 2008-541865 | 11/2008 |
| WO | WO 97/49355 | 12/1997 |
| WO | WO 00/53104 | 9/2000 |
| WO | WO 00/61034 | 10/2000 |
| WO | WO 01/35861 | 5/2001 |
| WO | WO 01/35870 | 5/2001 |
| WO | WO 01/72239 | 10/2001 |
| WO | WO 02/36048 | 5/2002 |
| WO | WO 03/028522 | 4/2003 |
| WO | WO 03/092554 | 11/2003 |
| WO | WO 2004/014257 | 2/2004 |
| WO | WO 2004/014474 | 2/2004 |
| WO | WO 2004/058097 | 7/2004 |
| WO | WO 2005/011534 | 2/2005 |
| WO | WO 2005/041810 | 5/2005 |
| WO | WO 2005/087140 | 9/2005 |
| WO | WO 2006/070372 | 7/2006 |
| WO | WO 2006/085304 | 8/2006 |
| WO | WO 2006/089236 | 8/2006 |
| WO | WO 2006/127765 | 11/2006 |
| WO | WO 2007/025028 | 3/2007 |
| WO | WO 2007/034488 | 3/2007 |
| WO | WO 2007/058857 | 5/2007 |
| WO | WO 2007/123658 | 11/2007 |
| WO | WO 2007/134290 | 11/2007 |
| WO | WO 2008/005535 | 1/2008 |
| WO | WO 2008/013915 | 1/2008 |
| WO | WO 2008/070797 | 6/2008 |
| WO | WO 2008/091515 | 7/2008 |
| WO | WO 2008/150529 | 12/2008 |
| WO | WO 2009/045331 | 4/2009 |
| WO | WO 2009/094500 | 7/2009 |
| WO | WO 2010/008549 | 1/2010 |
| WO | WO 2010/098857 | 9/2010 |

OTHER PUBLICATIONS

Boudjemline, Younes, MD, et al., "Steps Toward the Percutaneous Replacement of Atrioventricular Valves," JACC, vol. 46, No. 2, Jul. 19, 2005:360-5.

Leon, Martin B., MD, et al., "Transcatheter Aortic Valve Replacement in Patients with Critical Aortic Stenosis: Rationale, Device

(56) References Cited

OTHER PUBLICATIONS

Descriptions, Early Clinical Experiences, and Perspectives," Semin. Thorac. Cardiovasc. Surg. 18:165-174, 2006 in 10 pages, Applicant believes this may have been available as early as the Summer of 2006.

Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. of 2005.

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.

Walther, Thomas et al., "Transapical Approach for Sutureless Stent-Fixed Aortic Valve Implantation: Experimental Results," European Journal of Cardio-thoracic Surgery 29 (2006) 703-708, Applicant believes this may have been available as early as May of 2006.

European Extended Search Report for EP App. No. EP 06 82 7638, dated Feb. 28, 2013.

U.S. Appl. No. 14/197,590, filed Mar. 5, 2014, Ratz et al.
U.S. Appl. No. 14/197,639, filed Mar. 5, 2014, Ratz et al.
U.S. Appl. No. 14/197,690, filed Mar. 5, 2014, Ratz et al.
U.S. Appl. No. 29/484,001, filed Mar. 5, 2014, Pesce et al.
International Search Report and Written Opinion for PCT/US2006/043526, mailed Jun. 25, 2008.
European Examination Report for EP App. No. EP 06 827 638, dated Apr. 16, 2015.
U.S. Appl. No. 14/598,568, filed Jan. 16, 2015, Quadri et al.
U.S. Appl. No. 14/628,034, filed Feb. 20, 2015, Rabito et al.
U.S. Appl. No. 14/702,233, filed May 1, 2015, Arshad et al.
U.S. Appl. No. 14/716,507, filed May 19, 2015, Ratz et al.
U.S. Appl. No. 14/197,639, Prosthesis With Outer Skirt, filed Mar. 5, 2014.
U.S. Appl. No. 14/197,590, Prosthesis For Atraumatically Grasping Intralumenal Tissue and Methods of Delievery, filed Mar. 5, 2014.
U.S. Appl. No. 14/197,590, Prosthesis For Atraumatically Grasping Intralumenal Tissue and Methods of Delivery, filed Mar. 5, 2014.
U.S. Appl. No. 14/341,693, Systems and Methods for Sealing Openings in an Anatomical Wall, filed Jul. 25, 2014.
U.S. Appl. No. 14/313,160, Vascular Implant, filed Jun. 24, 2014.
U.S. Appl. No. 29/484,001, Wall Pattern for a Frame, filed Mar. 5, 2014.
U.S. Appl. No. 14/197,690, Prosthesis for Atraumatically Grasping Intralumenal Tissue and Methods of Delivery, filed Mar. 5, 2014.
U.S. Appl. No. 14/538,638, Vascular Implant and Delivery Method, filed Nov. 11, 2014.
U.S. Appl. No. 14/551,338, Delivery System for Vascular Implant, filed Nov. 24, 2014.
U.S. Appl. No. 14/598,568, Vascular Implant and Delivery Method, filed Jan. 16, 2015.
U.S. Appl. No. 14/702,233, Replacement Heart Valves, Delivery and Methods, filed May 1, 2015.
U.S. Appl. No. 14/716,507, Replacement Mitral Valve With Annular Flap, filed May 19, 2015.
U.S. Appl. No. 14/628,034, Prosthesis, Delivery Device and Methods of Use, filed Feb. 20, 2015.
U.S. Appl. No. 14/724,355, Prosthesis, Delivery Device and Methods of Use, filed May 28, 2015.
US 8,062,357, 11/2011, Salahieh et al. (withdrawn)

\* cited by examiner

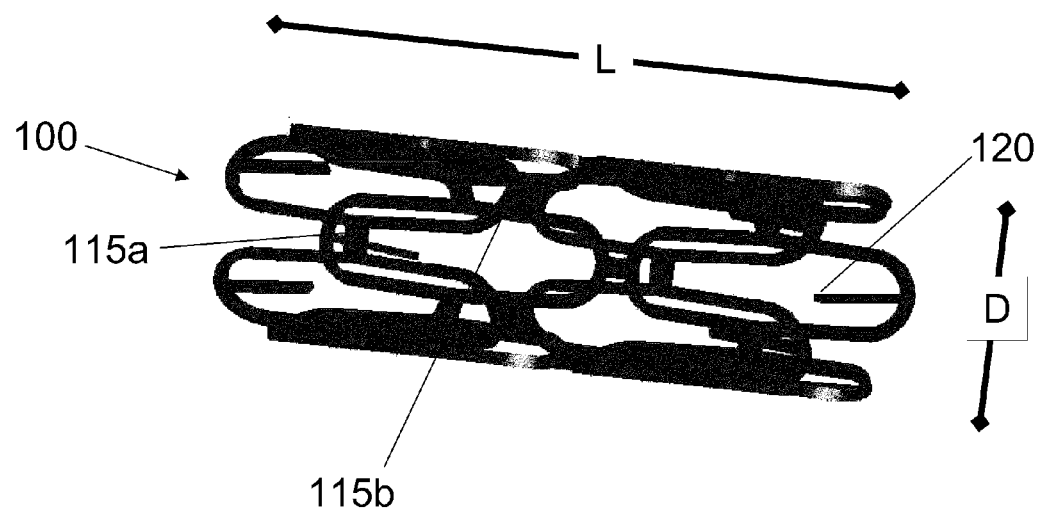
FIGURE 3
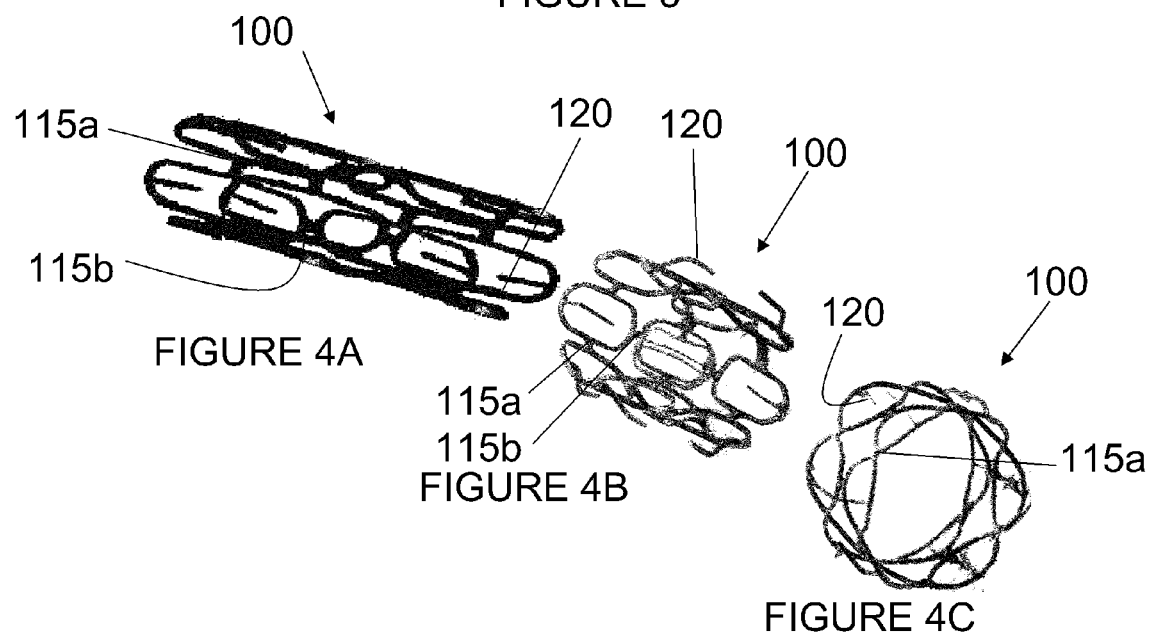
FIGURE 4A
FIGURE 4B
FIGURE 4C

FIGURE 5O

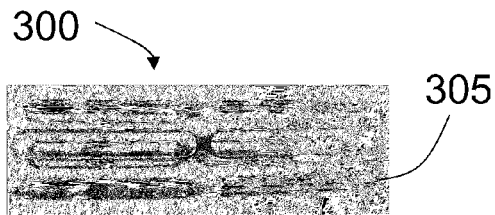
FIGURE 8A
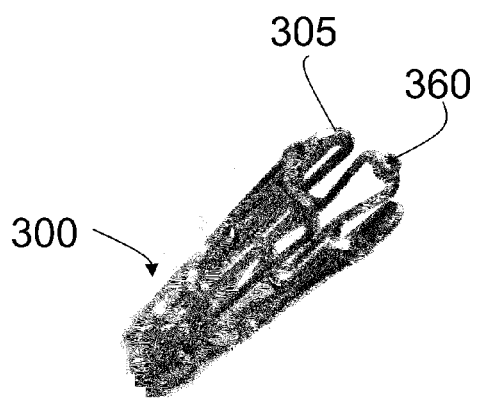
FIGURE 8B
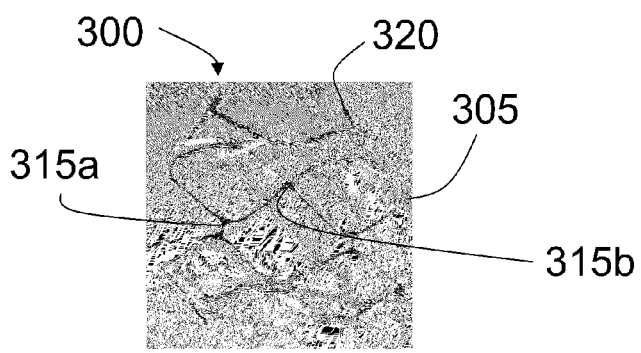
FIGURE 8C
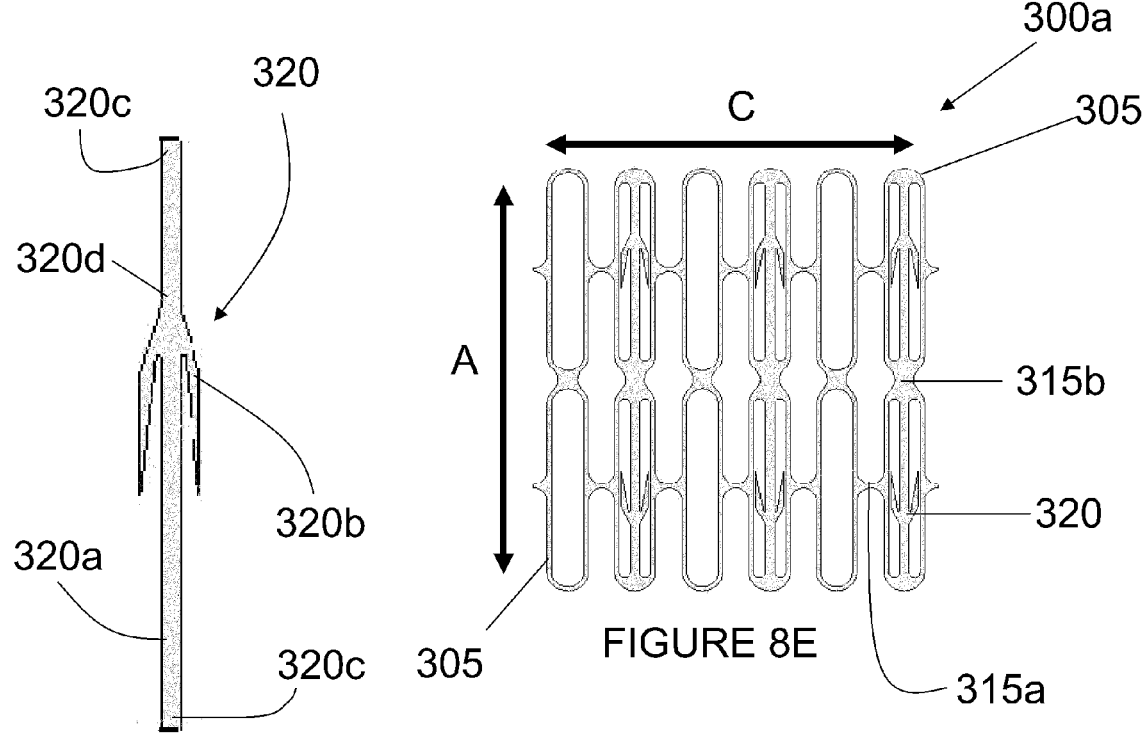
FIGURE 8D
FIGURE 8E

METHOD OF SECURING A PROSTHESIS

CROSS-REFERENCE TO RELATED APPLICATIONS

This application is a continuation of U.S. application Ser. No. 12/084,586, filed Apr. 13, 2009, now U.S. Pat. No. 8,092,520, which is a national stage of PCT/US2006/043526, filed Nov. 9, 2006, which claims the benefit of priority of U.S. Provisional Application No. 60/735,221, filed Nov. 10, 2005, all of which are hereby incorporated herein by reference in their entirety and are to be considered a part of this specification.

BACKGROUND

Field of the Invention

The present invention relates to a vascular balloon-expandable and/or self-expanding stent that can be used as a connecting/attaching mechanism for various kinds of vascular grafts or other prostheses in the vascular system of the human body.

SUMMARY OF THE INVENTION

It is a primary object of the present invention to provide a vascular balloon-expandable and/or self-expanding stent to facilitate efficient execution of simple and more complex vascular and cardiac procedures by less invasive and/or percutaneous techniques.

This and other objects of the present invention are achieved by an expandable vascular stent comprising an m×n array of ovals formed into a cylinder having a diameter, a circumference, an axis, and a length in the direction of the axis, where m is the number of columns of ovals in the circumferential direction and n is the number of rows of ovals in the axial direction. Connecting means located at rows 1 and n of the m×n array connect the cylinder to a surrounding body. The array of ovals can be of any size and number in a given stent.

The ovals have a short axis and a long axis, the short axis of the ovals extending in the circumferential direction and the long axis of the ovals extending in the axial direction. The cylinder is expandable from an initial diameter to a pre-determined final diameter, wherein an increase in the diameter of the stent results in a substantial decrease in the length of the stent to bring the prongs together to produce a connection to the body surrounding the stent.

The connecting means comprise a plurality of prongs extending inwardly from the outer ends of respective ovals in rows 1 and n of the m×n array. The prongs are arranged in facing pairs extending from ovals that are in alignment in the axial direction, and are approximately collinear in ovals having a common long axis, and approximately parallel in ovals having a common short axis.

Prior to expansion of the cylinder, the prongs substantially conform to the shape of the cylinder. As the stent expands, the distance between the prongs decreases and the prongs extend outwardly from the cylinder to engage the surrounding tissue.

Circumferential connectors connect adjacent ovals to each other in the circumferential direction and axial connectors connecting adjacent ovals to each other in the axial direction. The circumferential connectors and the axial connectors are positioned between the ovals coincident with the common short and long axes of the ovals, respectively.

The tube and the prongs can be made of surgical stainless steel, the tube being expandable using an angioplasty balloon; or the tube and the prongs can be made of a memory metal and the tube is self-expanding.

Other objects, features, and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 3 shows the stent form of FIG. 1 rolled into a stent.

FIGS. 4A-4C show the progression of deformation of the stent of FIG. 3 as it is stretched radially along its diameter.

FIG. 8A is a side elevational view of a third embodiment of the stent.

FIG. 8B is a perspective view of the stent of FIG. 8A.

FIG. 8C is a side elevational view of the stent of FIG. 8A in a deformed state after being stretched radially along its diameter.

FIG. 8D is an enlarged view of a prong of the stent of FIG. 8A.

FIG. 8E is a plan view of the stent form of FIG. 8A.

DETAILED DESCRIPTION OF THE PREFERRED EMBODIMENTS

Figure 1:
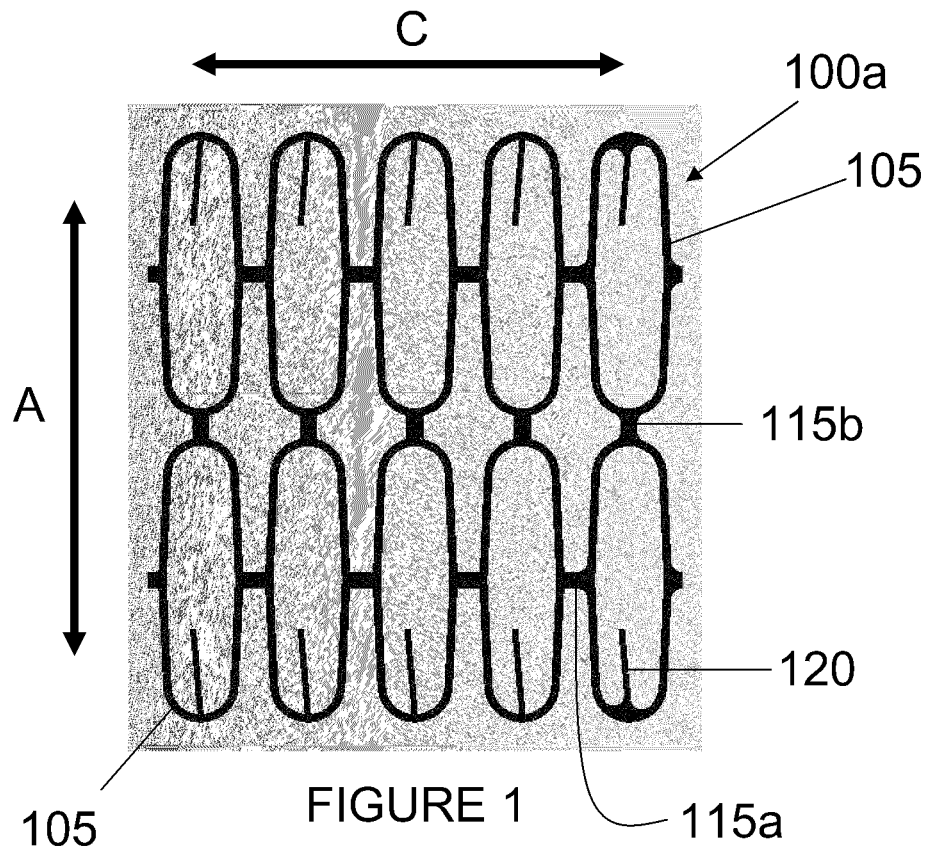
FIG. 1 shows a first embodiment of a stent form stamped from a piece of metal.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

As shown in FIGS. 3 and 4A-4C, a first embodiment of the device is a balloon expandable stainless steel stent 100 that can be expanded from an initial diameter (shown in FIG. 4A) to a pre-determined final diameter (shown in FIG. 4C) depending on the set dimensions of the balloon used to expand it. The configuration of the stent 100 is such that, with reference to FIG. 3, an increase in the diameter (D) of the stent will result in a substantial decrease in the length (L) of the stent.

To achieve this change in the shape and dimension of the stent 100, an m×n array 100a of ovals 105 is formed as shown in FIG. 1, where m is the number of columns of ovals in the circumferential direction C and n is the number of rows of ovals in the axial, or lengthwise, direction A, and where the short axis of the ovals 105 extends in the circumferential direction C and the long axis of the ovals 105 extends in the axial direction A. The array 100a shown in FIG. 1 is a 2×5 array. However, the array 100a can be any size greater than 1×1, depending on the desired size of the circumference and the length of the stent.

Figure 2:
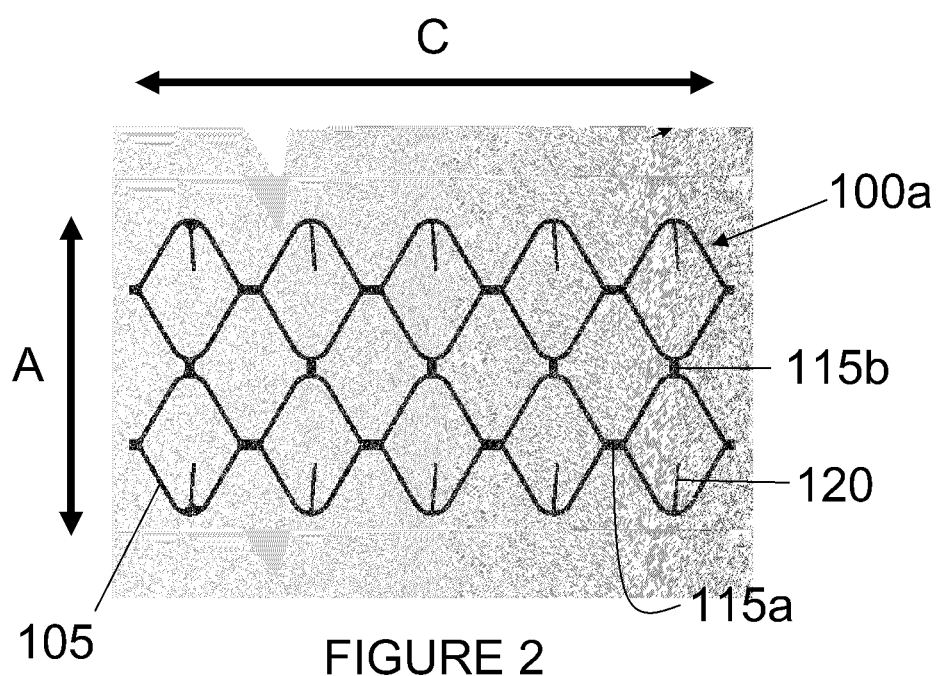
FIG. 2 shows the stent form of FIG. 1 stretched widthwise.

With reference to FIGS. 1 and 2, the array 100a of ovals 105 can be formed by stamping or electrical discharge machining from a sheet or tube of metal, preferably stainless steel. Adjacent ovals 105 are connected to each other in the circumferential direction C by connectors 115a and in the axial direction A by connectors 115b positioned between the ovals coincident with their common short and long axes, respectively.

At least some of the ovals 105 at the ends of the stent 100 (that is, the ovals 105 in rows 1 and n in the axial direction) have a prong 120 extending inwardly from their outer ends in approximate alignment with their longitudinal axes. The prongs 120 are placed in facing pairs extending from ovals 105 that are in alignment in the axial direction A. Thus, for ovals 105 having a common long axis, the prongs 120 are approximately collinear; while for ovals 105 having a common short axis, the prongs 120 are approximately parallel.

There may be intervening "blank" ovals 105 without any prongs 120, and which serve merely as spacers. The blank ovals 105 are utilized in some situations where more space is required between the connecting prongs 120.

If the array 100a of ovals 105 is formed from a sheet of metal, then the array 100a is rolled into a cylinder. The rolled cylinder and the stamped or machined tube have the general configuration of a stent 100, as shown in FIG. 4A, with the longitudinal axis of the cylinder being parallel to the long axes of the ovals 105.

In this embodiment, the prongs 120 are pre-bent. That is, at the time the stent 100 is formed, the prongs 120 are bent outwardly relative to the longitudinal axis of the cylinder, adjacent their attached ends, and also are bent inwardly relative to the longitudinal axis of the cylinder at a point offset from their free ends, in a reverse curve, so as to have a hook configuration.

An angioplasty balloon 130 is used to expand the undeployed stent 100 and to post the expanded stent 100 in the wall of an artery or other body cavity. When the balloon 130 is inflated, the ovals 105 expand in the direction of their short axes and contract along the direction of their long axes, deforming the ovals 105 into diamonds and causing a reduction in the length of the stent 100, as shown in FIGS. 4B and 4C. As also shown in FIGS. 4B and 4C, the deformation of the ovals 105 also causes the approximately collinear prongs 120 to draw closer together to engage the surrounding tissue and the approximately parallel prongs 120 to spread farther apart. This deformation of the ovals 105 and movement of the prongs 120 provide the connecting mechanism of the stent 100.

As illustrated in FIGS. 4B and 4C, when the frame is in an expanded configuration, there are a plurality of distal anchors, each of the distal anchors extending proximally to a proximal most portion that is positioned radially outward from the frame. There are also a plurality of proximal anchors, each of which extend distally to a distal most portion that is positioned radially outward from the frame. The proximal most portions of the distal anchors extend in a direction that is more parallel with a longitudinal axis of the frame than with a transverse axis perpendicular to the longitudinal axis of the frame, and the distal most portions of the proximal anchors extend in a direction that is more parallel with the longitudinal axis than with a transverse axis perpendicular to the longitudinal axis of the frame. The proximal anchors are connected to the frame only at locations on the frame proximal to the distal most portions, and the distal anchors are connected to the frame only at locations on the frame distal to the proximal most portions. The distal most portions of the proximal anchors and the proximal most portions of the distal anchors are spaced apart by less than two cell lengths or less than one cell length when the frame is in an expanded configuration. When the frame is in an expanded configuration, at least some of the anchoring portions of at least one of the pluralities of proximal anchors and distal anchors curve radially outward before extending respectively, distally or proximally, in an axial direction approximately parallel with each other and with the longitudinal axis.

The angioplasty balloon 130 is the correct size and shape to expand the stent 100 to the desired size and shape. The undeployed stent 100 is loaded over the balloon 130 of a conventional balloon catheter 132 and inserted into the artery or other body cavity according to conventional medical procedure. Inflating the balloon 130 deploys (opens) the stent 100 (that is, causes an increase in its diameter and a decrease in its length), which remains expanded to keep the artery or body cavity open. A high-pressure balloon 130 allows the physician to fully expand the stent 100 until it is in full contact with the wall of the artery or body cavity. A low compliance balloon 130 is used so that the stent 100 and the artery or body cavity will not be over-expanded, and so that the balloon 130 will not dog-bone and over-expand the artery or body cavity on either end of the stent 100. The stent 100 stays in position after the balloon 130 is deflated and removed from the body.

In instances when the stent 100 is self-expanding, i.e. made from memory metal, then upon deployment the stent 100 takes its predetermined configuration.

Figure 5A:
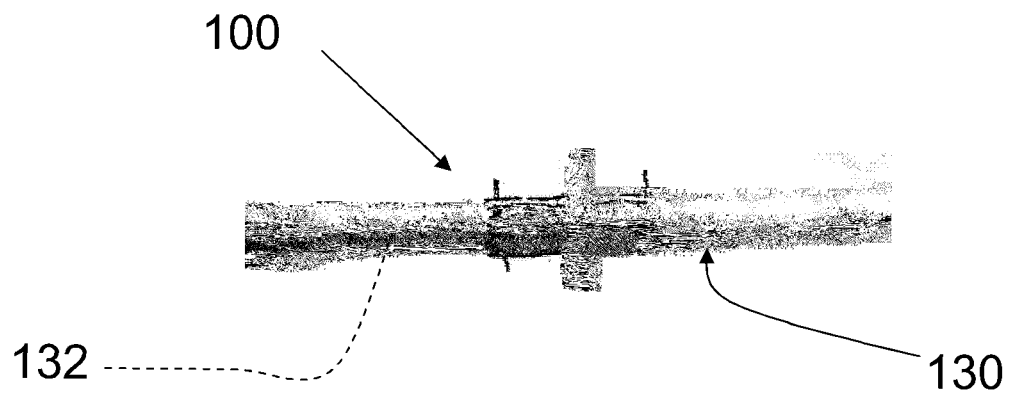
FIGS. 5A-5Q show the steps in the expansion of the stent of FIG. 3 in an artery or other body cavity.
Figure 5B:
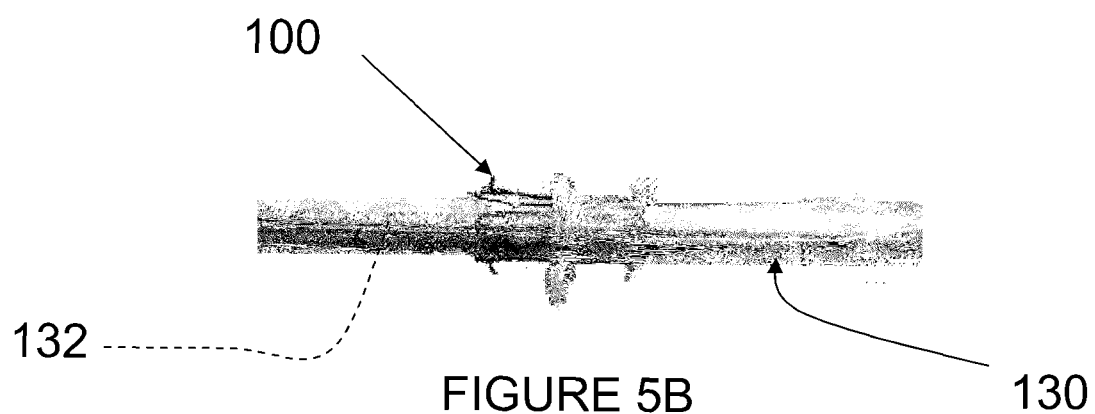
Figure 5C:
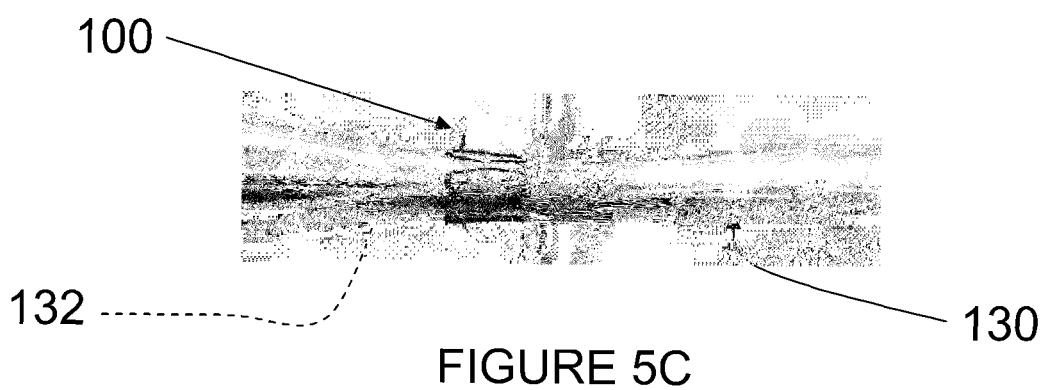
Figure 5D:
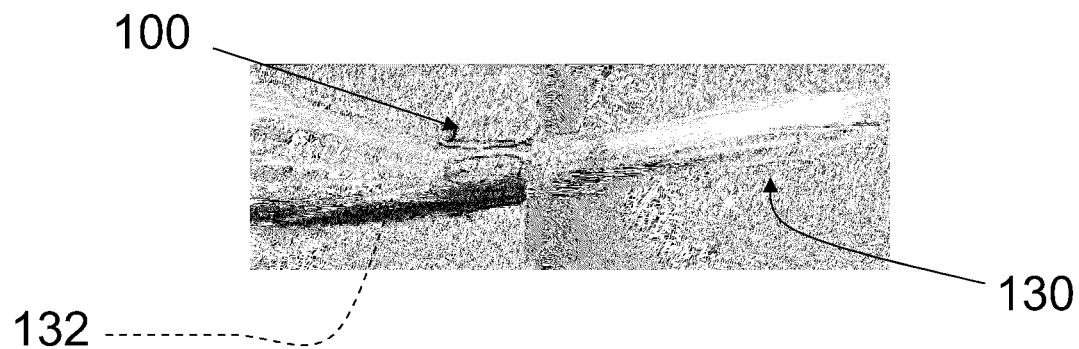
Figure 5E:
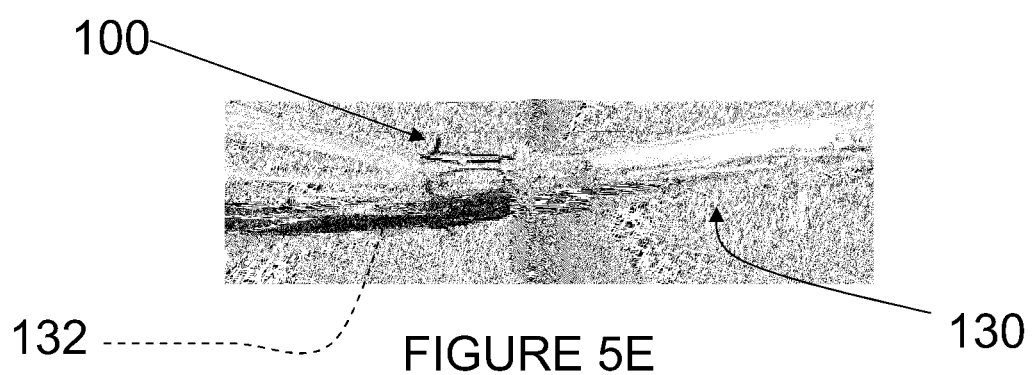
Figure 5F:
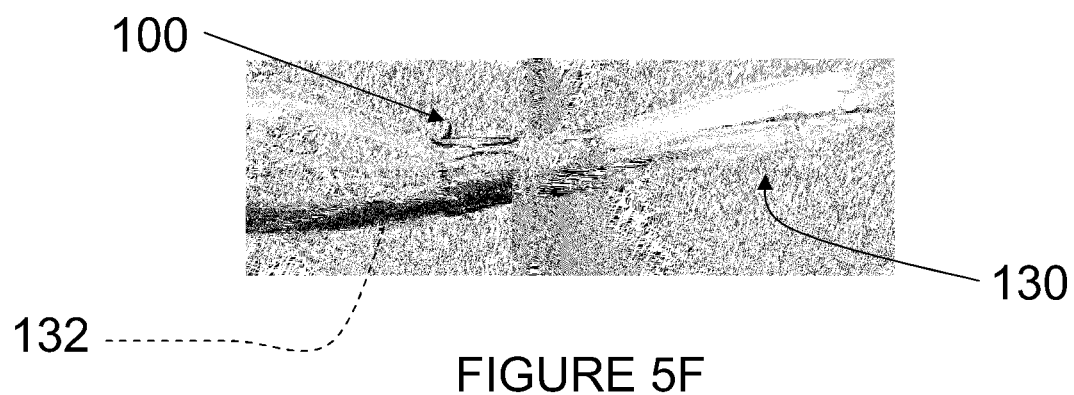
Figure 5G:
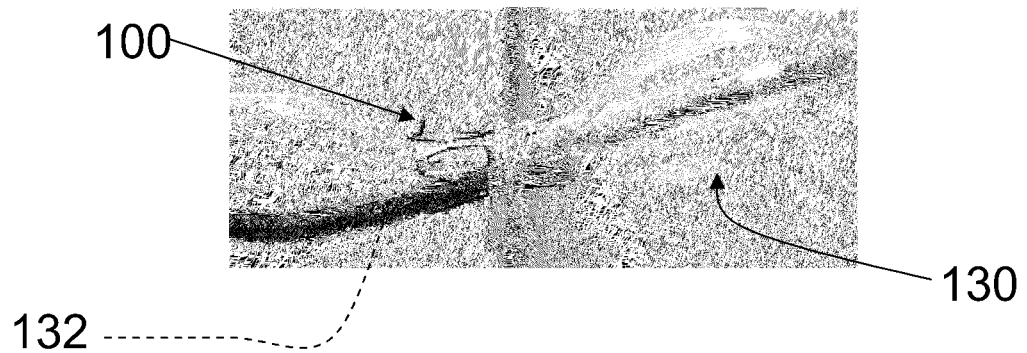
Figure 5H:
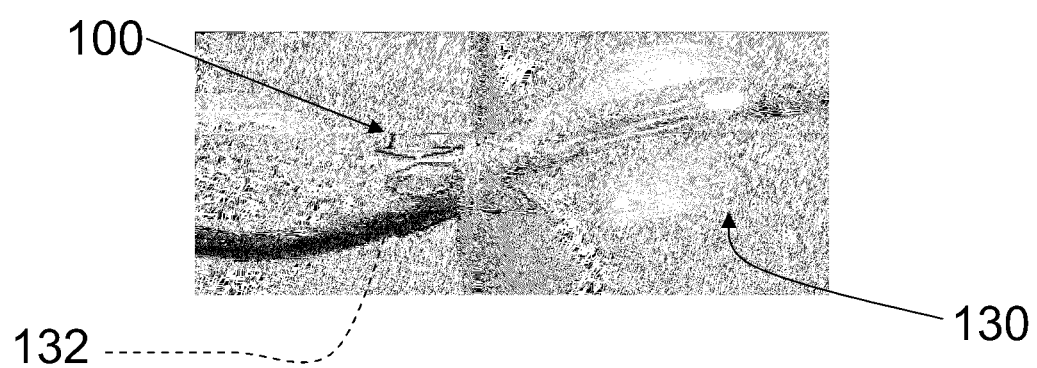
Figure 5I:
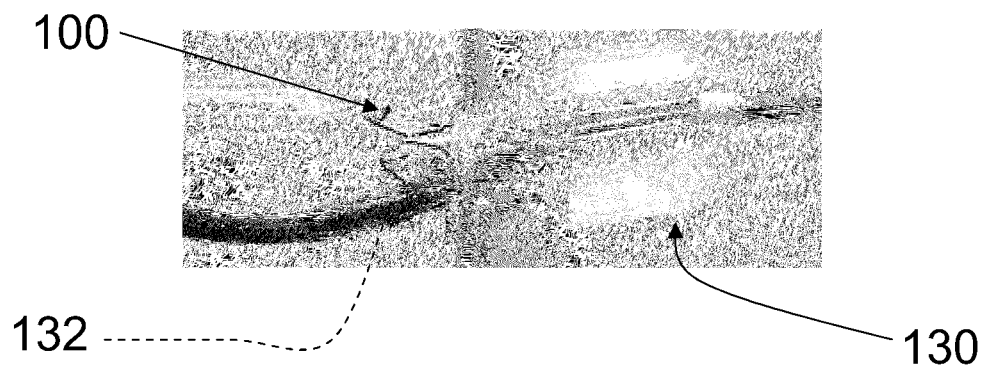
Figure 5J:
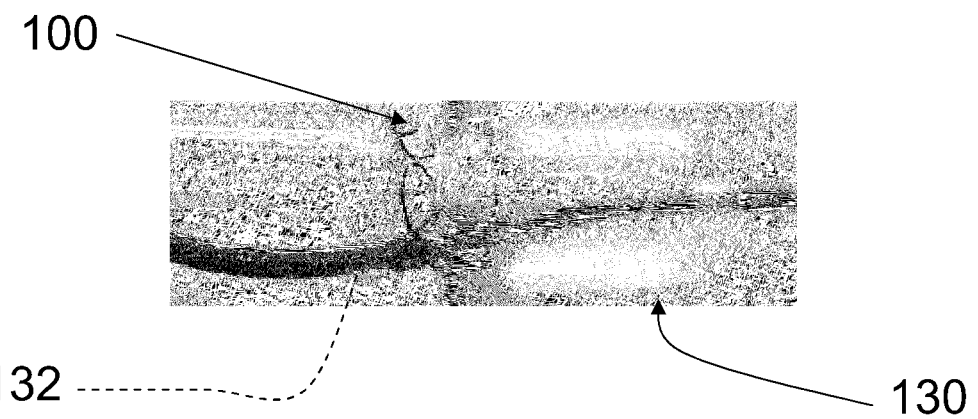
Figure 5K:
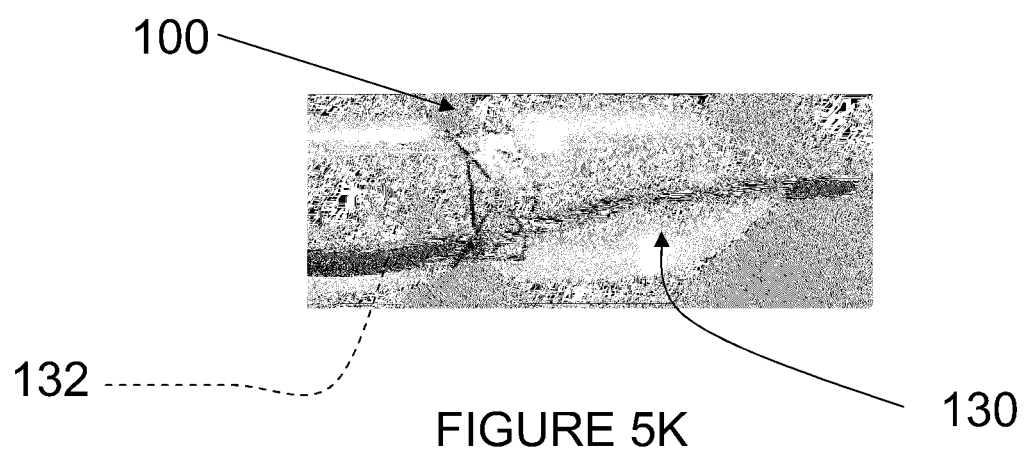
Figure 5L:
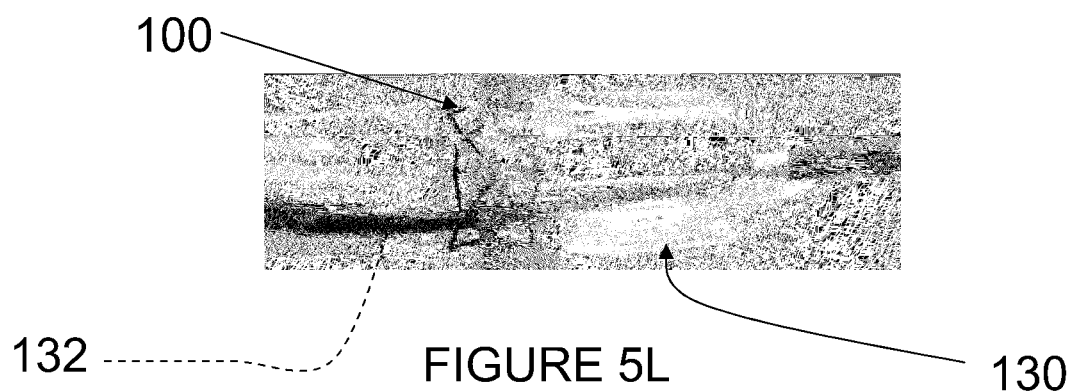
Figure 5M:
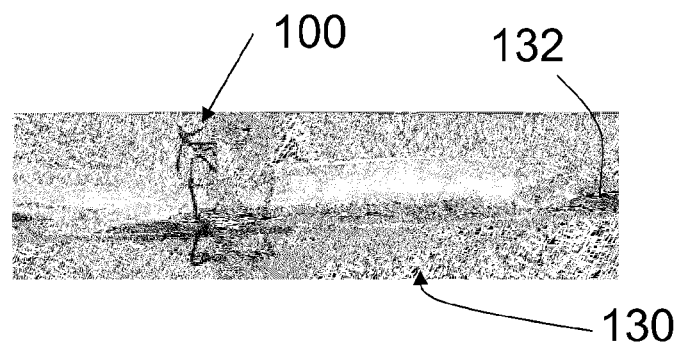
Figure 5N:
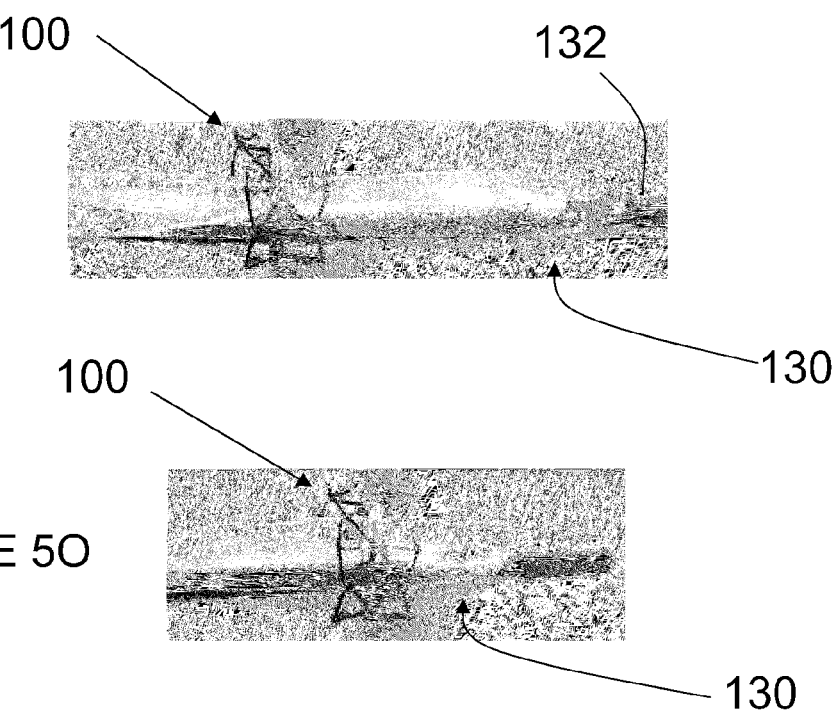
Figure 5P:
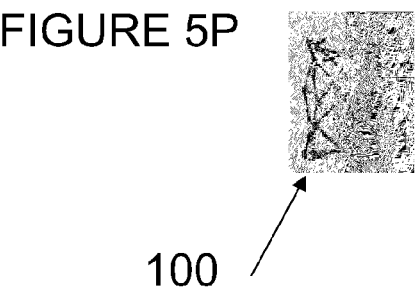
Figure 5Q:
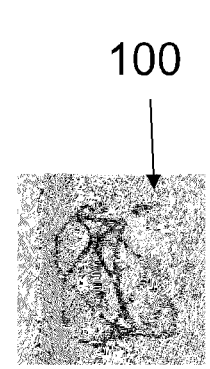

FIGS. 5A-5Q show the steps in the expansion of the stent of FIG. 3 in an artery or other body cavity.

The stent 100 in accordance with the present invention can also be of use as a versatile connector in clinical settings in which it can be pre-attached to a side wall of another prosthesis, such as an endo-luminal graft. It can also be used as a connector to connect main and branch endo-aortic grafts for branch graft repair, as described in my co-pending U.S. patent application Ser. No. 10/960,296, filed Oct. 8, 2004.

The stent 100 in accordance with the present invention can further be used in conjunction with percutaneous heart valve technology. In a percutaneous heart valve procedure, a collapsed percutaneous heart valve 125 is mounted on a balloon-expandable stent 100 and threaded through the patient's circulatory system via a catheter to the aortic valve from either an antegrade approach (in which the patient's septum and mitral valve are crossed to reach their native aortic valve) or a retrograde approach (in which the percutaneous heart valve 125 is delivered directly to the aortic valve through the patient's main artery). Once in the aortic valve, the percutaneous heart valve 125 is expanded by a balloon catheter to push the patient's existing valve leaflets aside and anchor inside the valve opening.

Figure 6A:
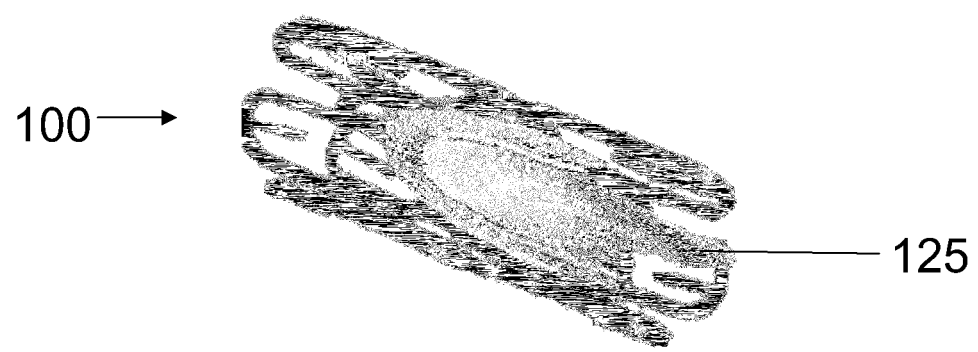
FIG. 6A is a perspective view, partially cut away, of a collapsed prosthetic heart valve loaded in an undeployed stent in accordance with the present invention.
Figure 6B:
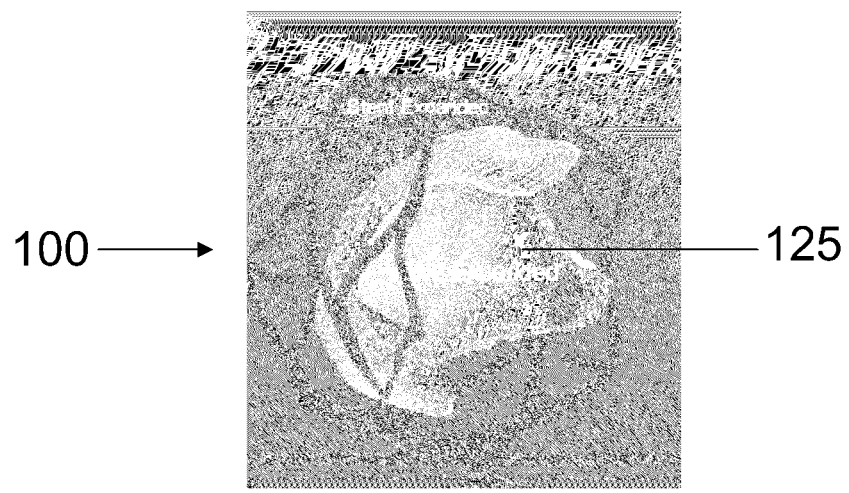
FIG. 6B is a perspective view, partially cut away, of the prosthetic heart valve and stent of FIG. 6A in their expanded conditions.

As shown in FIG. 6A, the percutaneous heart valve 125 in a collapsed state can be seated inside the undeployed stent 100 in accordance with the present invention, which in turn is loaded over the balloon of a conventional balloon catheter, as previously described. Once the valve 125 and stent 100 are positioned in the desired location, the balloon 130 is inflated, causing the valve 125 and the stent 100 to expand, as shown in FIG. 6B. The valve 125 is fixed in position by the mechanism provided by the stent 100.

Figure 7A:
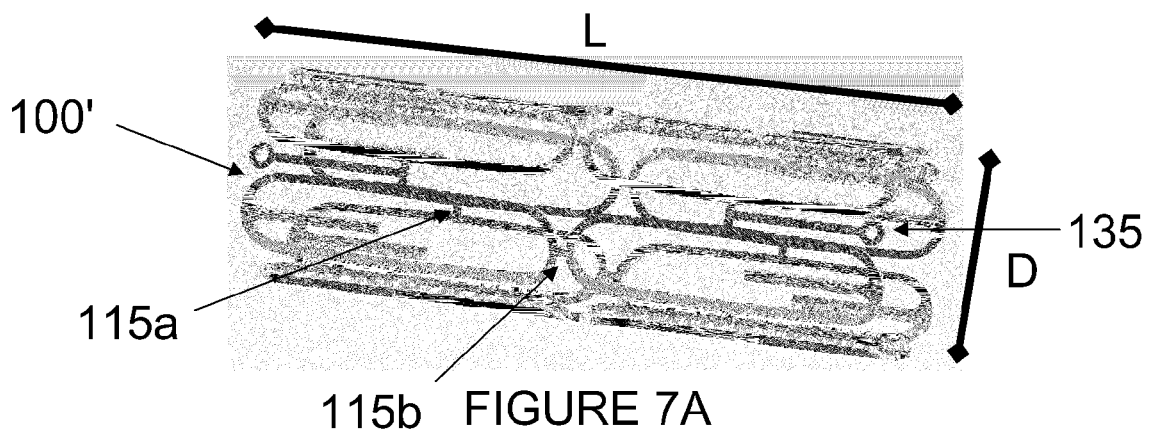
FIGS. 7A-7C show the progression of deformation of a second embodiment of the stent as it is stretched radially along its diameter.
Figure 7B:
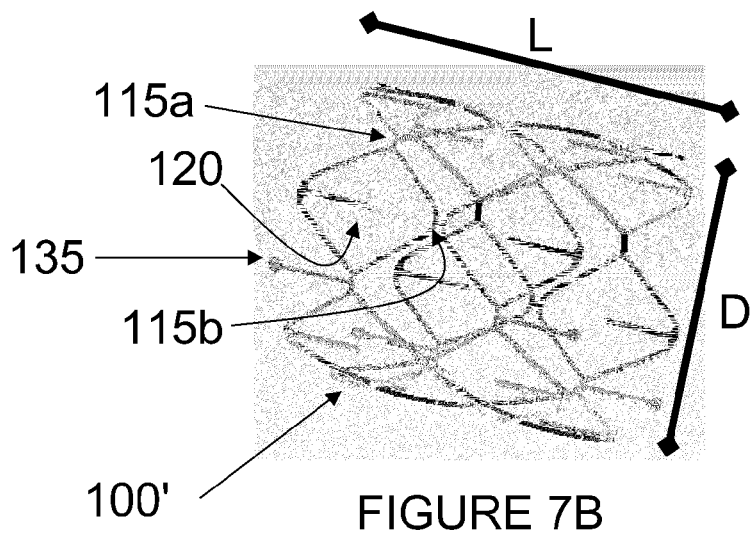
Figure 7C:
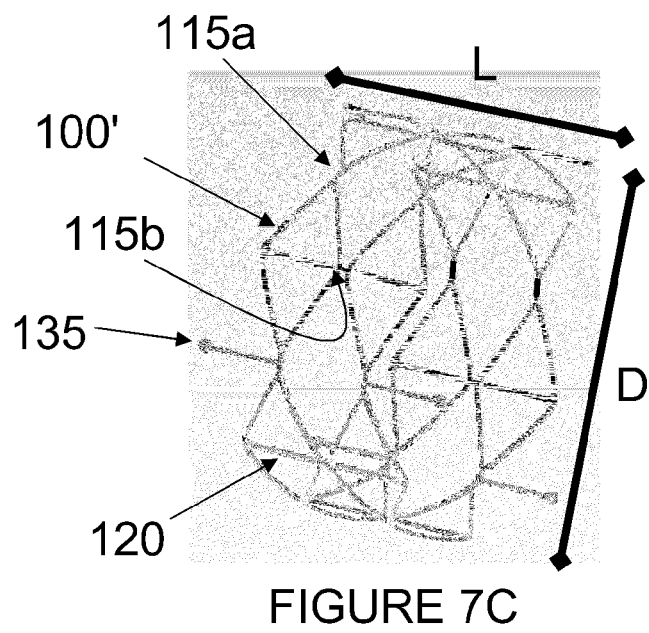

A second embodiment of the stent 100', and the progression of its deformation as it is stretched radially along its diameter, is shown in FIGS. 7A-7C. In this alternate embodiment, the stent 100' is similar to the stent 100, but has additional prongs 135 extending from and perpendicular to the connectors 115a positioned between the ovals 105, and parallel to the longitudinal axis of the stent 100'. These prongs 135 are for the purpose of attaching the stent 100' to, for example, a branch graft or a valve.

A third embodiment of the stent 300 is shown in its undeployed state in FIGS. 8A and 8B, and in its deployed state after being stretched radially along its diameter in FIG. 8C. In the third embodiment, the stent 300 is formed of an m×n array 300a of ovals 305 formed as shown in FIG. 8E. With reference to FIG. 8D, the array 300a of ovals 305 can be formed by laser-cutting a sheet or tube of metal, preferably stainless steel or a memory metal. Adjacent ovals 305 are connected to each other in the circumferential direction C by connectors 315a and in the axial direction A by connectors 315b positioned between the ovals coincident with their common short and long axes, respectively.

At least some of the ovals 305 at the ends of the stent 300 (that is, the ovals 305 in rows 1 and n in the axial direction) have a prong 320 extending inwardly from their outer ends in approximate alignment with their longitudinal axes. The prongs 320 are placed in facing pairs extending from ovals 305 that are in alignment in the axial direction A. Thus, for ovals 305 having a common long axis, the prongs 320 are approximately collinear; while for ovals 305 having a common short axis, the prongs 320 are approximately parallel. The prongs 350 are bifurcated, providing two point penetration for better purchase.

Referring now to FIGS. 8D and 8E, in the embodiment of FIGS. 8A-8C, each prong 320 includes a spine 320a extending the length of the long axis of the oval 305 and a furcation 320b on either side of the spine 320a at a location between the ends of the spine 320. The spine 320a has two end hinge points 320c at the ends thereof and one intermediate hinge point 320d at the base of the furcations 320b. The amount by which the ovals 305 are foreshortened and the angle of the prongs 320 (that is, the angle of the furcations 320b) can be adjusted by varying the location of the furcations 320b and the intermediate hinge point 320d relative to the ends of the spines 320 and the end hinge points 320c.

There may be intervening "blank" ovals 305 without any prongs 320, and which serve merely as spacers. The blank ovals 305 are utilized in some situations where more space is required between the connecting prongs 320. At least some of the ovals 305 at one end of the stent 300 can include a docking socket 360 (shown in FIG. 8C) for mating to the cardiac locking pin of a valve frame.

Figure 9A:
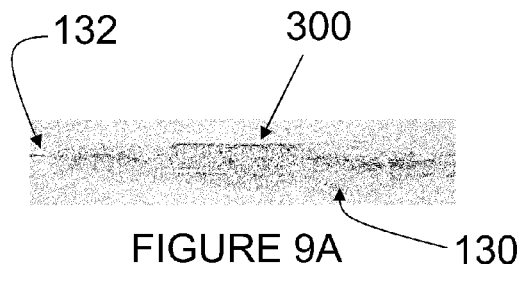
FIGS. 9A-9G show the steps in the expansion of the stent of FIG. 8A in an artery or other body cavity.
Figure 9B:
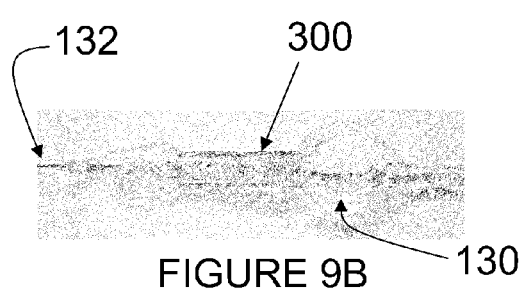
Figure 9C:
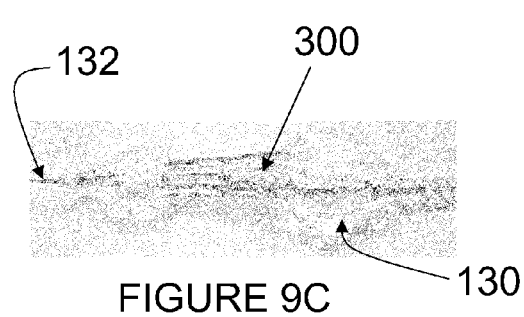
Figure 9D:
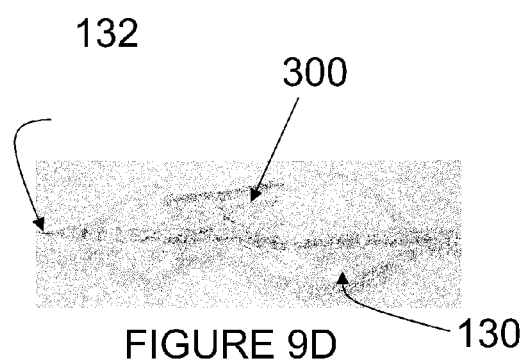
Figure 9E:
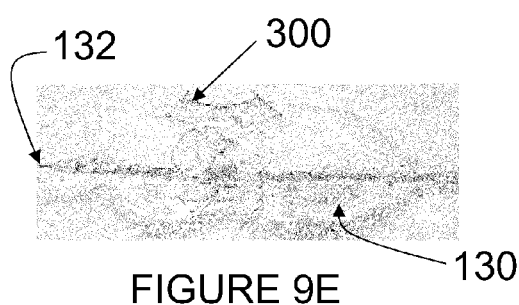
Figure 9F:
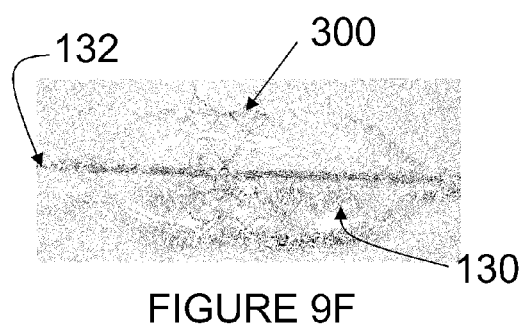
Figure 9G:
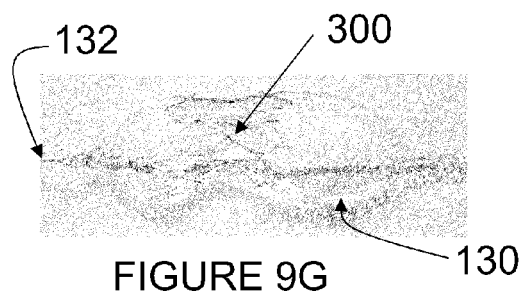

FIGS. 9A-5Q show the steps in the expansion of the stent of FIGS. 8A-8C in an artery or other body cavity, using an angioplasty balloon. The undeployed stent 300 is loaded over the balloon 130 of a conventional balloon catheter 132 and inserted into the artery or other body cavity according to conventional medical procedure. As the balloon 130 inflates, the ovals 305 foreshorten in the axial direction, causing the spines 320a of the prongs 320 to bend at the hinges 320c and 320d and the consequent activation of the prongs 320. As the balloon 130 continues to inflate, the angles assumed by the spines 320a at their hinges reach their maximums, bringing opposing furcations 320b together to engage the tissue therebetween.

Figure 10A:
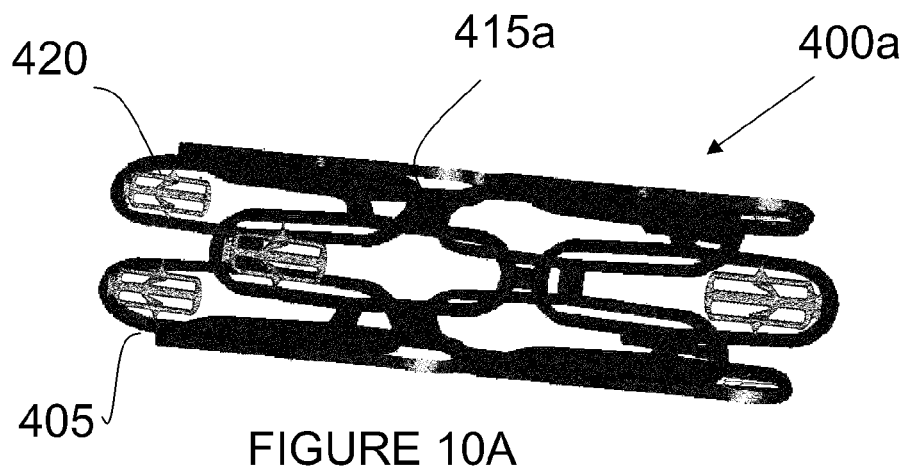
FIG. 10A is a perspective view of a fourth embodiment of the stent.
Figure 10B:
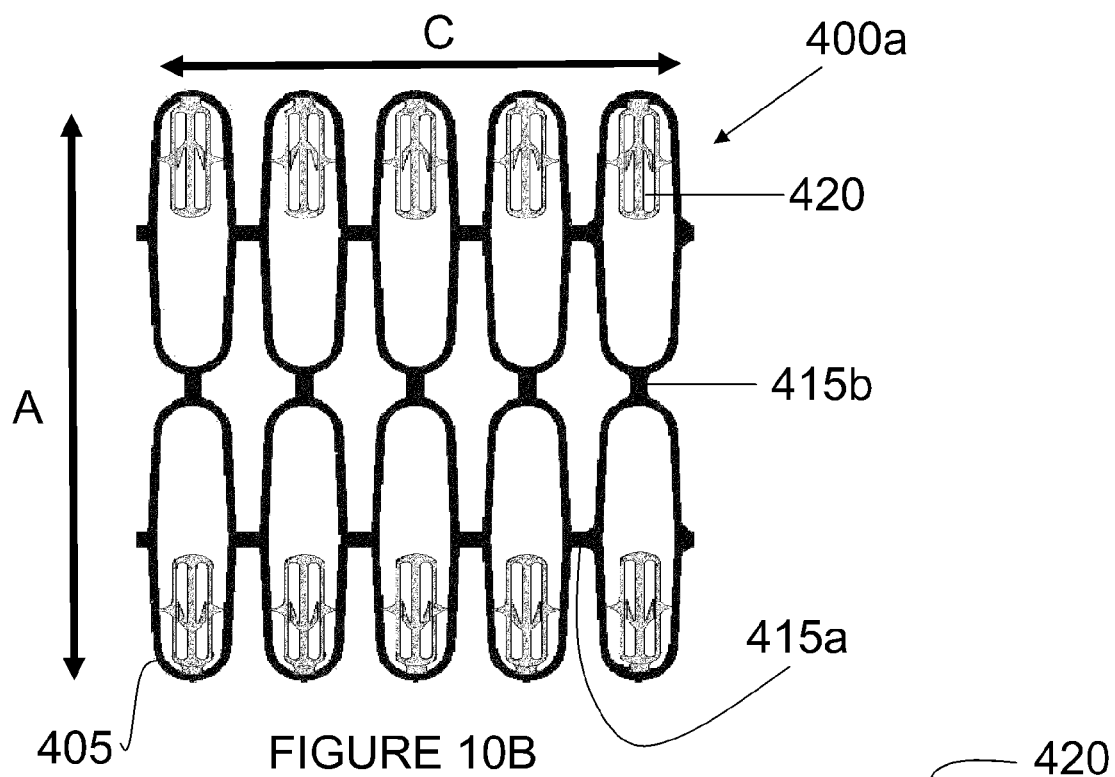
FIG. 10B is a plan view of the stent form of FIG. 10A.

Referring now to FIGS. 10A and 10B, there is shown a fourth embodiment of the stent 400. In the fourth embodiment, the stent 400 is formed of an m×n array 400a of ovals 405. With reference to FIG. 10B, the array 400a of ovals 405 can be formed by laser-cutting a sheet or tube of metal, preferably stainless steel. Adjacent ovals 405 are connected to each other in the circumferential direction C by connectors 415a and in the axial direction A by connectors 415b positioned between the ovals coincident with their common short and long axes, respectively.

At least some of the ovals 405 at the ends of the stent 400 (that is, the ovals 405 in rows 1 and n in the axial direction) have a prong 420 extending inwardly from their outer ends in approximate alignment with their longitudinal axes. The prongs 420 are placed in facing pairs extending from ovals 405 that are in alignment in the axial direction A.

Figure 10C:
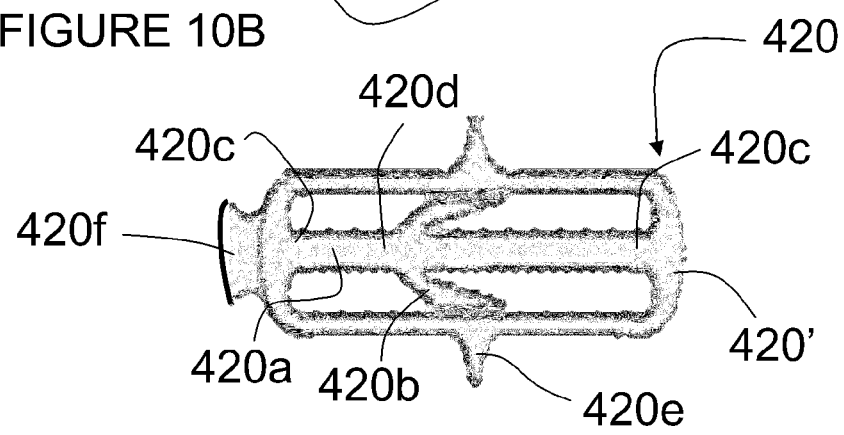
FIG. 10C is an enlarged view of the prong of the stent of FIG. 10A.

As shown in FIG. 10C, each prong 420 has substantially the same configuration as an oval 305 and a prong 320 of the third embodiment, described above. That is, each prong 420 includes an oval frame 420', a spine 420a extending the length of the long axis of the oval frame 420', and a furcation 420b on either side of the spine 420a at a location between the ends of the spine 420. The spine 420a has two end hinge points 420c at the ends thereof and one intermediate hinge point 420d at the base of the furcations 420b.

The oval frames 420' are connected at their short axes to the ovals 405 by connectors 420e, and are connected at one end of their long axes to the ovals 405 by a connector 420f. Thus, as the ovals 405 foreshorten, the oval frames 420' also foreshorten. The amount by which the oval frames 420' are foreshortened and the angle of the furcations 420b can be adjusted by varying the location of the furcations 420b and the intermediate hinge point 420d relative to the ends of the spines 420 and the end hinge points 420c. Preferably, the prongs 420 are formed by laser cutting.

As with stent 300, stent 400 is loaded over the balloon 130 of a conventional balloon catheter 132 and inserted into the artery or other body cavity according to conventional medical procedure. As the balloon 130 inflates, the ovals 405 and the oval frames 420' foreshorten in the axial direction, causing the spines 420a of the prongs 420 to bend at the hinges 420c and 420d and the consequent activation of the prongs 420. As the balloon 130 continues to inflate, the angles assumed by the spines 420a at their hinges reach their maximums, bringing opposing furcations 420b together to engage the tissue therebetween.

There may be intervening "blank" ovals 405 without any prongs 420, and which serve merely as spacers. The blank ovals 405 are utilized in some situations where more space is required between the connecting prongs 420. At least some of the ovals 405 at one end of the stent 400 can include a docking socket (not shown) similar to the docking socket 360 shown in FIG. 8C, for mating to the cardiac locking pin of a valve frame.

Modifications and variations of the above-described embodiments of the present invention are possible, as appreciated by those skilled in the art in light of the above teachings. It is therefore to be understood that the invention may be practiced otherwise than as specifically described.

What is claimed is:

1. A method of securing a prosthesis to a native heart valve, comprising:
   delivering a prosthesis into a patient, the prosthesis comprising:
      an expandable frame extending along a longitudinal axis between a proximal end and a distal end, the expandable frame comprising a first and second row of cells;
      a plurality of spaced-apart proximal anchors connected to the frame at the first row of cells;
      a plurality of spaced-apart distal anchors connected to the frame at the second row of cells; and
      a replacement valve seated within the frame; and
   expanding the frame within the native heart valve of the patient with the replacement valve seated within the frame, wherein expansion of the frame causes the proximal anchors and the distal anchors to draw closer together with body tissue positioned between the proximal anchors and the distal anchors, wherein when the frame is in an expanded configuration:
      each distal anchor of the plurality of distal anchors extends proximally to a proximal most portion of the distal anchor that is positioned radially outward from the frame;
      the proximal most portions of the distal anchors extend in a direction that is more parallel with the longitudinal axis than with a transverse axis perpendicular to the longitudinal axis;
      the proximal most portions of the distal anchors are spaced apart from the proximal anchors by less than two cell lengths; and
      at least one of the distal anchors bends radially outwardly before bending to extend longitudinally toward the plurality of spaced-apart proximal anchors.

2. The method of claim 1, wherein when the frame is in an expanded configuration, each proximal anchor of the plurality of proximal anchors extends distally to a distal most portion of the proximal anchor that is positioned radially outward from the frame.

3. The method of claim 2, wherein when the frame is in an expanded configuration, each proximal anchor extends distally in a direction that is more parallel with the longitudinal axis than with a transverse axis perpendicular to the longitudinal axis.

4. The method of claim 2, wherein the proximal most portions of the distal anchors and the distal most portions of the proximal anchors are spaced apart by less than one cell length when the frame is in the expanded configuration.

5. The method of claim 1, wherein the distal anchors are connected to the frame only at locations on the frame distal to the proximal most portions of the distal anchors.

6. The method of claim 1, wherein distal most portions of the proximal anchors and proximal most portions of the distal anchors are generally collinearly aligned.

7. The method of claim 1, wherein expanding the frame comprises expanding the frame by self-expansion.

8. The method of claim 1, wherein expanding the frame further comprises foreshortening at least a portion of the frame.

9. The method of claim 1, wherein each distal anchor of the plurality of distal anchors is connected to the frame in a distal portion of a cell, and wherein with respect to such cells having distal anchors, expanding the frame causes the distal portion of such cells to extend further radially outward than a proximal portion of such cells.

10. The method of claim 1, wherein after expanding the frame within the native heart valve of the patient, body tissue spaced radially outward from the frame and positioned between the proximal anchors and the distal anchors is pinched between the proximal and distal anchors.

11. The method of claim 1, wherein the proximal anchors and the distal anchors are atraumatic.

12. The method of claim 1, wherein at least one of the distal anchors extends from a distal portion of a cell.

13. The method of claim 12, wherein the at least one distal anchor extends from a corner of the distal portion of the cell.

14. A method of securing a prosthesis to a native heart valve, comprising:
   delivering a prosthesis into a patient, the prosthesis comprising:
      an expandable frame extending along a longitudinal axis between a proximal end and a distal end, the expandable frame comprising a plurality of cells;
      a proximal anchoring portion connected to the frame;
      a plurality of spaced-apart distal anchors connected to the frame; and
      a replacement valve seated within the frame; and
   expanding the frame within the native heart valve of the patient with the replacement valve seated within the frame, wherein expansion of the frame causes the proximal anchoring portion and the distal anchors to draw closer together with body tissue positioned between the proximal anchoring portion and the distal anchors, wherein when the frame is in an expanded configuration:
      each distal anchor of the plurality of distal anchors extends proximally to a proximal most portion of the distal anchor that is positioned radially outward from the frame;
      the proximal most portions of the distal anchors extend in a direction that is more parallel with the longitudinal axis than with a transverse axis perpendicular to the longitudinal axis;
      the proximal most portions of the distal anchors are spaced apart from the proximal anchoring portion by less than two cell lengths; and
      each distal anchor of the plurality of distal anchors is connected to the frame within a cell; and
      with respect to such cells having distal anchors, expanding the frame causes a distal portion of such cells to extend further radially outward than a proximal portion of such cells and wherein each distal anchor extends only from the distal portion of such cells in a direction generally parallel with the longitudinal axis toward the proximal anchoring portion, and
      wherein each such cell comprises only one anchor.

15. The method of claim 14, wherein the distal anchors are atraumatic.

16. The method of claim 14, wherein after expanding the frame within the native heart valve of the patient, body tissue spaced radially outward from the frame and positioned between the proximal anchoring portion and the distal anchors is pinched between the proximal anchoring portion and the distal anchors.

17. The method of claim 14, wherein each distal anchor of the plurality of distal anchors is generally equally spaced between sides of corresponding cells.

18. The method of claim 14, wherein at least one distal anchor extends from a corner of the distal portion of a corresponding cell.

19. The method of claim 18, wherein the at least one distal anchor extends from a distal most corner of the corresponding cell.

20. The method of claim 14, wherein at least one of the distal anchors bends radially outwardly before bending to extend longitudinally toward the proximal anchoring portion.

\* \* \* \* \*